United States Patent [19]

Pistorius

[11] Patent Number: 4,680,147

[45] Date of Patent: Jul. 14, 1987

[54] PROCESS FOR THE ISOLATION UNDER MILD CONDITIONS OF PARAFFINSULFONATE AND SULFURIC ACID FROM REACTION MIXTURES FROM PARAFFIN SULFOXIDATION

[75] Inventor: Rudolf Pistorius, Hünstetten, Fed. Rep. of Germany

[73] Assignee: Hoechst Aktiengesellschaft, Fed. Rep. of Germany

[21] Appl. No.: 804,312

[22] Filed: Dec. 2, 1985

Related U.S. Application Data

[63] Continuation of Ser. No. 629,994, Jul. 12, 1984, abandoned.

[30] Foreign Application Priority Data

Jul. 15, 1983 [DE] Fed. Rep. of Germany ....... 3325516

[51] Int. Cl.$^4$ ............................................ C07C 143/02
[52] U.S. Cl. .............................. 260/513 R; 260/504 S
[58] Field of Search .......................... 260/513 R, 504 S

[56] References Cited

U.S. PATENT DOCUMENTS

| | | | |
|---|---|---|---|
| 3,423,454 | 1/1969 | Marrian | 260/513 R |
| 4,177,208 | 12/1979 | Boy et al. | 260/513 R |
| 4,178,307 | 12/1979 | Boy et al. | 260/513 R |

*Primary Examiner*—Alan Siegel
*Attorney, Agent, or Firm*—Connolly and Hutz

[57] ABSTRACT

A process for the isolation under mild conditions of paraffinsulfonate from the aqueous reaction mixtures which result from the sulfoxidation of n-paraffins, from which sulfur dioxide has been removed by degassing, and which contain higher molecular weight sulfonic acids, sulfuric acid, n-paraffins and water, in which aliphatic alcohols having 2 to 8 carbon atoms and organic solvents, which are insoluble in water or miscible with water to only a limited extent, are simultaneously allowed to act on the reaction mixtures, the aqueous phase which has separated out and contains sulfuric acid is removed, and the product phase containing paraffinsulfonates is neutralized, evaporated, and the remaining paraffin is driven out with superheated steam.

5 Claims, No Drawings

PROCESS FOR THE ISOLATION UNDER MILD CONDITIONS OF PARAFFINSULFONATE AND SULFURIC ACID FROM REACTION MIXTURES FROM PARAFFIN SULFOXIDATION

This case is a continuation of my copending application, Ser. No. 629,994, filed July 12, 1984, now abandoned.

The aqueous solutions of paraffinsulfonic acids obtainable by sulfoxidation of n-paraffins by, for example, the process in German Pat. No. 910,165 also contain sulfur dioxide, sulfuric acid and hydrotropically dissolved paraffins. In order to isolate from reaction mixtures of this type utilizable paraffinsulfonic acids or paraffinsulfonates of good quality, i.e. products which are as low as possible in sulfuric acid and salts, are pale and are essentially odorless, it is necessary to remove sulfur dioxide, sulfuric acid and paraffins as quantitatively and under as mild conditions as possible. The products of paraffin sulfoxidation already start to decompose at temperatures above 50° C., and this is shown in the appearance of the acid reaction mixture by a discoloration from water-white via yellowish and brown to finally jet black. Even though the amount of paraffinsulfonic acid which is decomposed by the action of temperature is still relatively low as long as the acid reaction mixtures are not exposed to temperatures above 100° C. for a prolonged period, nevertheless even a small proportion of decomposed products requires, because of their color intensity, a considerable expenditure on bleach if acceptably pale products are desired.

It has been found that, in contrast, those salts of the paraffinsulfonic acids which have a weakly alkaline reaction are relatively stable. Temperatures below 200° C., even when the duration of heating is prolonged, lead to only quite inconsiderable discoloration, and higher temperatures up to about 260° C. result only in discoloration which can still readily be removed again with small amounts of bleaching agent.

Thus, care must be taken that no discoloration occurs even during the first step in working up the reaction mixtures from paraffin sulfoxidation, the degassing to remove sulfur dioxide. If the degassing is carried out under a gentle vacuum, only a brief period of heating at about 85° C. is required to achieve virtually complete elimination of sulfur dioxide. Noticeable decomposition, i.e. the occurrence of a deepening in color of the reaction mixture, in this process can be prevented by then immediately cooling the reaction mixture down again to room temperature.

In respect of the quality of the paraffinsulfonate, it would be favorable to neutralize the reaction mixture immediately after degassing. However, because of the large amounts of alkali necessary to neutralize the sulfuric acid and because of the considerable losses of paraffinsulfonate which occur on filtering off the alkali metal sulfate, a procedure of this type is uneconomic and not industrially practicable.

Thus, after the removal of the sulfur dioxide from the reaction mixture, an attempt must be made before the neutralization to remove the sulfuric acid from the mixture as completely as possible and without decomposing the paraffinsulfonic acid. In the known processes which aim at this goal, the procedure is generally such that the degassed sulfoxidation mixture is treated with a suitable organic solvent in order to bring about separation into an organic phase, which contains the paraffinsulfonic acids, and an aqueous phase, which contains the sulfuric acid as far as possible in the form of an aqueous solution which is generally 10 to 25% strength. The two phases are then separated, and the organic phase is further worked up to isolate the paraffinsulfonic acids or their salts. Thus, the addition of organic solvents which are insoluble in water or are miscible with water to only a limited extent, such as, for example, benzene, chlorobenzene, cyclohexane, carbon tetrachloride, chloroform, methylene chloride and the like, to remove sulfuric acid from the sulfoxidation mixture has already been disclosed in German Patent Application F 3718, 120 which was published on Jan. 29, 1953. According to German Offenlegungsschrift No. 2,730,245, ethers, such as, for example, diethyl ether or di-n-butyl ether, and, according to German Offenlegungsschrift No. 2,745,691, ketones or esters, and, according to German Offenlegungsschrift No. 2,139,477, alcohols having at least 4 carbon atoms, are also used for the same purpose.

None of these known processes for removing sulfuric acid at low temperatures has hitherto been able to succeed industrially, since either the proportion of the sulfuric acid separated out is too low, the expense of removing the solvent by distillation is too high.

It has now been found, surprisingly, that the aqueous sulfuric acid is separated out of the degassed reaction mixture from paraffin sulfoxidation to a particularly large extent at low temperature when the reaction mixture is mixed with a polar alcohol having 2 to 8 carbon atoms and an organic solvent which is of low polarity and is insoluble in water or is miscible with water to a limited extent.

Thus the invention relates to a process for the isolation under mild conditions of paraffinsulfonate from the reaction mixtures which result from the sulfoxidation of n-paraffins, from which sulfur dioxide has been removed by degassing, and which contain higher molecular weight paraffinsulfonic acids, sulfuric acid, n-paraffin and water, which process comprises allowing aliphatic alcohols having 2 to 8 carbon atoms and organic solvents which are insoluble in water or are miscible with water to only a limited extent to act on such reaction mixtures at the same time, separating off the aqueous phase containing sulfuric acid, and neutralizing the phase containing paraffinsulfonic acid, evaporating it and driving out the remaining paraffin from the residue using superheated steam.

The starting materials which can be used for the process of the present invention are the reaction mixtures from the known sulfoxidation processes, from which sulfur dioxide has been removed by degassing under mild conditions, and which represent aqueous mixtures of higher molecular weight paraffinsulfonic acids, sulfuric acid and n-paraffin. For example, the reaction mixtures obtainable by the process of German Pat. No. 735,096 can be used. It is also possible to start from reaction mixtures as are obtained on sulfoxidation using peroxides, ozone or even γ-radiation, for example by the process of German Pat. No. 1,139,116. The present process is preferably based on the aqueous reaction mixtures which result from the sulfoxidation of n-paraffins having chain lengths with about 7 to 20, preferably 13 to 18, carbon atoms, and which, during the sulfoxidation, separate out from the excess paraffin as a heavier, clear phase.

According to the invention, the aliphatic alcohols and the less polar organic solvents can be mixed either simultaneously or in arbitrary sequence with the reaction mixtures from which sulfur dioxide has been removed. The amount of aliphatic alcohols to be added depends on the composition of the reaction mixture and is about 5 to 80% by weight, preferably 8 to 50% by weight, in particular 10 to 45% by weight, relative to the weight of the reaction mixture used. The amount of the weakly polar organic solvent to be added is in the range of about 10 to 200% by weight, preferably of 20 to 150% by weight, in particular 30 to 70% by weight, relative to the weight of the reaction mixture used. However, the amount of the weakly polar organic solvent used for this should preferably be equal to or larger than, in particular about twice, the amount of the alcohol used.

The alcohol and organic solvent act on the reaction mixture at low temperatures, advantageously in the range from about 5° to 50° C., preferably at about 10° to 30° C. The development of the two phases takes place within 2 hours at the most, but generally after only 15 to 30 minutes. The phase-separation time can be considerably shortened by suitable measures, for example by passing the mixture through a droplet separator. Even filtration through a paper filter or glass wool brings about considerably more rapid separation, so that the aqueous phase containing sulfuric acid can be separated out after only about 10 minutes.

It is possible to use as less polar solvents, which are insoluble in water or are miscible with water to a limited extent, in the process of the invention those which are inert toward the constituents of the reaction mixture under the conditions of work-up. Suitable organic solvents are those whose boiling points are in the range from about 20° to 150° C., preferably from 30° to 100° C. Examples of suitable solvents of this type are carbon tetrachloride, chloroform, 1,2-dichloroethane, 1,1,2-trichlorotrifluoroethane and, in particular, methylene chloride. Examples of suitable aliphatic alcohols are ethanol, propanols, butanols, hexanols and 2-ethylhexanol. n-Hexanol and 2-ethylhexanol are preferably used.

After removing the aqueous sulfuric acid, the product phase which contains the paraffinsulfonic acids, alcohol and organic solvent, and still contains paraffin, is neutralized at temperatures below 55° C., preferably below 50° C., advantageously in such a manner that, with vigorous stirring, alkali and the product phase are introduced simultaneously. The rate of metering-in for this is adjusted so that the pH, measured, for example, with a calibrated glass pH electrode, in the mixture of the two liquids is always above 7, in particular above 10.5, so that the paraffinsulfonate which is obtained when work-up is complete has a neutral or weakly alkaline pH. However, for the neutralization it is also possible initially to introduce the entire amount of alkali, and to allow the product phase to run in until the desired pH above pH 7 or above pH 10.5 has been reached. It is possible in principle, even though less advantageous, to reverse the process, i.e. to add the alkali to the product solution which has been initially introduced.

Any desired alkalis can be used to neutralize the paraffinsulfonic acids. It is possible to employ sodium or potassium hydroxide, advantageously in the form of concentrated aqueous solutions; however, it is also possible to use sodium or potassium carbonate or sodium or potassium bicarbonate.

After the neutralization, the product phase is evaporated in a manner known per se, by single-stage or multistage distillation, to remove the alcohol, organic solvent and paraffin, finally the remaining paraffin and, where appropriate, solvent being driven out by superheated steam at 180° to 280° C. The melt of paraffinsulfonate thus obtained can then be adjusted to the desired concentration by the addition of water at 100° to 160° C. under appropriate pressure, it being possible to add 0.01 to 1% by weight, in particular 0.1 to 0.3% by weight, of hydrogen peroxide to the water to eliminate any traces of color or odor.

It is regarded as a considerable advantage of the process according to the invention that, by using it, it is possible to obtain pale-colored products which have a faint odor and are low in salts in an economic manner, this being particularly brought about by the sulfuric acid being substantially separated out under extremely mild conditions. The substantial separation-out of the sulfuric acid achieved in the process of the invention by the action of alcohols and less polar organic solvents is surprising for the reason that each of these solvents alone per se brings about only a far less complete or no separation out at all of sulfuric acid, so that this effect of the combination was not to be expected. Furthermore, because the energy of vaporization of the weakly polar organic solvents is considerably lower than that of alcohols, it proves to be advantageous that amounts of alcohol below 40% by weight, and in suitable cases below 20% by weight, (relative to the amount of the reaction mixture) even suffice to obtain paraffinsulfonates containing less than 5% of inorganic salts (relative to material with detergent activity).

EXAMPLE 1

Straight-chain paraffin hydrocarbons having 14 to 17 carbon atoms were reacted in a sulfoxidation apparatus with sulfur dioxide and oxygen in the presence of water, irradiating with UV light at 30° to 40° C. An aqueous reaction mixture was obtained, and sulfur dioxide was removed from this by heating it to 85° C. under a gentle vacuum. Following this, the reaction mixture was composed of 42.3% water, 7.33% sulfuric acid, 21.25% paraffinsulfonic acids and 29.12% paraffins. In accordance with the following table, n-hexanol alone, methylene chloride alone, and mixtures of n-hexanol and methylene chloride were added to separate samples of this reaction mixture. After settling at 23° C. for 12 hours, the aqueous sulfuric acid which had separated out was removed. The resulting product phases were adjusted to pH 12.5 by introduction together with sodium hydroxide solution, and then evaporated at temperatures of 160° C. (±20° C.) until a melt was obtained, and this was stripped with superheated steam until paraffin no longer distilled over. Then, at 120° C., sufficient water was added to produce paraffinsulfonate pastes containing 60% by weight of paraffinsulfonate, and the content of sodium sulfate in these was determined.

The following contents of sodium sulfate as a function of the amounts of solvents (related to the reaction mixture) were found:

TABLE 1

Content of $Na_2SO_4$ in % by weight (relative to 60% material with detergent activity)

| Amount of n-hexanol added (% by weight) | Amount of methylene chloride added (% by weight) | | | | | | |
|---|---|---|---|---|---|---|---|
| | 0 | 10 | 15 | 20 | 25 | 30 | 40 |
| 0 | 27.8 | n.d. | n.d. | n.d. | n.d. | 18.99 | 16.55 |
| 10 | 5.51 | 4.1 | 3.1 | 2.84 | n.d. | 2.37 | n.d. |
| 15 | 3.35 | 2.6 | 2.03 | 1.89 | 1.84 | 1.59 | n.d. |
| 20 | 2.73 | 2.04 | 1.56 | 1.47 | 1.39 | 1.26 | n.d. |
| 25 | 2.09 | 1.78 | 1.28 | 1.40 | 1.30 | 1.17 | n.d. |
| 30 | 1.73 | 1.6 | 1.15 | 1.09 | 0.88 | 0.79 | n.d. |
| 35 | 2.00 | 0.96 | 1.07 | 0.96 | 0.86 | n.d. | n.d. |
| 40 | 2.01 | 0.91 | 1.21 | 1.12 | 1.22 | n.d. | n.d. | n.d. = not determined

EXAMPLE 2

Isobutanol and methylene chloride or isobutanol and 1,1,2-trichlorotrifluoroethane (F 113) were added in accordance with the following Table 2 to samples of a reaction mixture, of the same composition as indicated in Example 1, from which sulfur dioxide has been removed. After working up to give 60% strength paraffinsulfonate pastes as indicated in Example 1, the following parts by weight of sodium sulfate (relative to 60% material with detergent activity) were found in the resulting products:

TABLE 2

Content of $Na_2SO_4$ in % by weight

| Amount of isobutanol added (% by weight) | Amount of methylene chloride added (% by weight) | | Amount of F 113 added (% by weight) | |
|---|---|---|---|---|
| | 0 | 30 | 50 | 30 | 50 |
| 10 | 7.29 | n.d. | 2.22 | n.d. | 4.57 |
| 15 | 4.20 | 2.01 | n.d. | 3.33 | n.d. | n.d. = not determined

I claim:

1. A process for the isolation under mild conditions of paraffinsulfonate from the aqueous reaction mixtures which result from the sulfoxidation of n-paraffins, from which sulfur dioxide has been removed by degassing, and which contain higher molecular weight sulfonic acids, sulfuric acid, n-paraffins and water, which process comprises allowing at least one aliphatic alcohol having 2 to 8 carbon atoms and at least one less-polar solvent to act on such reaction mixtures at the same time, removing the aqueous phase which has separated out and contains sulfuric acid, and neutralizing the product phase containing paraffinsulfonates, evaporating it and driving out the remaining paraffin using superheated steam; said less polar solvents being carbon tetrachloride, chloroform, 1,2-dichloroethane, 1,1,2-trichloro-trifluoroethane, or methylene chloride.

2. The process as claimed in claim 1, wherein the action of said aliphatic alcohols and said less polar solvents to separate out the aqueous sulfuric acid takes place at temperatures below 50° C.

3. The process as claimed in claim 1 wherein said aliphatic alcohols and said less polar solvents are used in the alcohol:less-polar solvent weight ratio 1:1 to 1:2.

4. The process as claimed in claim 1, wherein said less polar solvent consists essentially of methylene chloride.

5. The process as claimed in claim 1, wherein said aliphatic alcohol consists essentially of hexanol or 2-ethylhexanol.

* * * * *